(12) United States Patent
Choi et al.

(10) Patent No.: US 8,859,954 B1
(45) Date of Patent: Oct. 14, 2014

(54) METHOD FOR DISCRIMINATIMG SITOSTEROLEMIA USING A DRIED BLOOD SPOT

(71) Applicant: Korea Institute of Science and Technology, Seoul (KR)

(72) Inventors: Man Ho Choi, Seoul (KR); Bong Chul Chung, Namyangju (KR); Hyun Hwa Son, Seoul (KR); Eun Gyong Yoo, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 14/045,359

(22) Filed: Oct. 3, 2013

(30) Foreign Application Priority Data

May 7, 2013 (KR) .................. 10-2013-0051426

(51) Int. Cl.
*B01D 59/44* (2006.01)
*G01N 30/72* (2006.01)
*G01N 33/92* (2006.01)

(52) U.S. Cl.
CPC ............ *G01N 33/92* (2013.01); *G01N 30/7206* (2013.01)
USPC ............ 250/282; 250/281; 250/288; 436/173

(58) Field of Classification Search
CPC .......... G01N 2500/00; G01N 33/6848; G01N 30/7206; G01N 2800/50; G01N 33/92
USPC ........................................ 250/281, 282, 288
See application file for complete search history.

(56) References Cited

U.S. PATENT DOCUMENTS 5,965,449 A * 10/1999 Novak ............................. 436/71
2003/0049730 A1 * 3/2003 Hobbs et al. .................. 435/69.1

OTHER PUBLICATIONS

G. Salen et al., "Sitosterolemia," *Journal of Lipid Research*, vol. 33, 1992, pp. 945-955.
M. Barbi et al., "Diagnosis of congenital CMV infection via dried blood spots," *Reviews in Medical Virology*, vol. 16, pp. 385-392.
W. Li et al., "Dried blood spot sampling in combination with LC-MS/MS for quantitative analysis of small molecules," *Biomedical Chromatography*, vol. 24, pp. 49-65.

* cited by examiner

*Primary Examiner* — Michael Maskell
(74) *Attorney, Agent, or Firm* — Staas & Halsey LLP

(57) ABSTRACT

Disclosed herein is a method for discriminating sitosterolemia by simultaneously measuring relative concentrations of phytosterol and cholesterol metabolism-related compounds in a blood spot on the paper. According to the present disclosure, sitosterolemia may be quickly discriminated with high accuracy by simple sample collecting using a trace amount of blood spot stained on a paper, and it may be used for newborn screening and preschool children, particularly patients with xanthoma.

6 Claims, 6 Drawing Sheets

Cholesterol

Sitosterol

Stigmasterol

Campesterol

METHOD FOR DISCRIMINATIMG SITOSTEROLEMIA USING A DRIED BLOOD SPOT

CROSS-REFERENCE TO RELATED APPLICATIONS

This application claims priority under 35 U.S.C. §119 to Korean Patent Application No. 10-2013-0051426, filed on May 7, 2013, in the Korean Intellectual Property Office, the disclosure of which is incorporated herein by reference in its entirety.

TECHNICAL FIELD

The present disclosure relates to a method for discriminating sitosterolemia by simultaneously measuring concentrations of phytosterols and cholesterol metabolism-related compounds.

BACKGROUND

Sitosterolemia is a rare disease, only about 80 cases of which have been reported worldwide (see data from Office of Rare Diseases Research, National Institute of Health). It is an inherited lipid metabolic disorder mainly occurring in growing children by genetic modification, characterized by hyperabsorption of phytosterols such as sitosterol, campesterol and stigmasterol in the small intestine and significantly decreased biliary excretion of dietary sterols in the liver leading to accumulation of the phytosterols in the body. Thus, blood concentrations of sitosterol and stigmasterol in sitosterolemia patients are 10 to 25 times higher than in normal individuals [*J. Lipid Res.*, 1992, 33: 945-955], leading to hypercholesterolemia or xanthoma and early atherosclerosis.

However, there is no specific treatment for sitosterolemia except taking drugs such as statin inhibiting cholesterol synthesis or ezetimibe inhibiting cholesterol absorption, and dietary treatment reducing the intake of foods rich in phytosterols is common. There is a risk that sitosterolemia may be misdiagnosed as child hypercholesterolemia or atherosclerosis with immunologic methods generally used in hospitals because structures of phytosterols are very similar with that of cholesterol. Accordingly, accurate and prompt diagnosis is of utmost importance to discriminate sitosterolemia from hypercholesterolemia or atherosclerosis. Accordingly, accurate diagnosis using precise analyzing methods such as chromatography-mass spectrometry is in demand, but there is inconvenience that a large amount of blood should be collected and the blood should be separated into serum or plasma by centrifugation when measuring the blood concentrations of phytosterols.

The dried blood spot has been mainly used for newborn screening and diagnosis of metabolic disorders [*Rev. Mde. Virol.*, 2006, 16: 385-392; *Biomed. Chromatogr.* 2010, 24: 49-65]. The blood spot needs only a very small amount of blood. Accordingly, the dried blood spot has advantages of a simpler sample collection and an easier storage or transfer. However, when using the blood spot, it is difficult to determine the exact amount of the collected sample used in a test. Accordingly, because the absolute concentration of metabolites in the blood spot cannot be measured, standardized discriminating techniques, for example, evaluating metabolic ratios between compounds after measuring concentrations of all compounds exhibiting metabolic correlations, are required.

Considering the above, the present inventors tried to accomplish a quick and accurate method for discriminating sitosterolemia by metabolic ratios between compounds, which are obtained by simultaneously measuring concentrations of cholesterol metabolism-related compounds as well as phytosterols such as sitosterol, stigmasterol and campesterol, contained in the blood spot, using gas chromatography-mass spectrometry.

Throughout this application, various patents and publications are referenced and citations are provided in parentheses. The disclosure of these patents and publications in their entities are hereby incorporated by references into this application in order to more fully describe this disclosure and the state of the art to which this disclosure pertains.

SUMMARY

The present inventors have conducted intensive researches to develop a method for simply discriminating metabolic disorder of sitosterol, one of phytosterols. As a result, the present disclosure was completed by founding that when analyzing relative concentrations of phytosterols and cholesterol metabolism-related compounds in one drop of blood spot on a paper by gas chromatography-mass spectrometry, the sitosterolemia may be quickly discriminated with high accuracy.

Accordingly, an object of the present disclosure is to provide a method for discriminating sitosterolemia by simultaneously measuring concentrations of phytosterols and cholesterol metabolism-related compounds.

Detailed objects and features of the present disclosure will become apparent from the detailed description to follow and together with the appended claims and drawings.

BRIEF DESCRIPTION OF THE DRAWINGS

The above and other objects, features and advantages of the present disclosure will become apparent from the following description of certain exemplary embodiments given in conjunction with the accompanying drawings, in which.

DETAILED DESCRIPTION OF EMBODIMENTS

Figure 1:
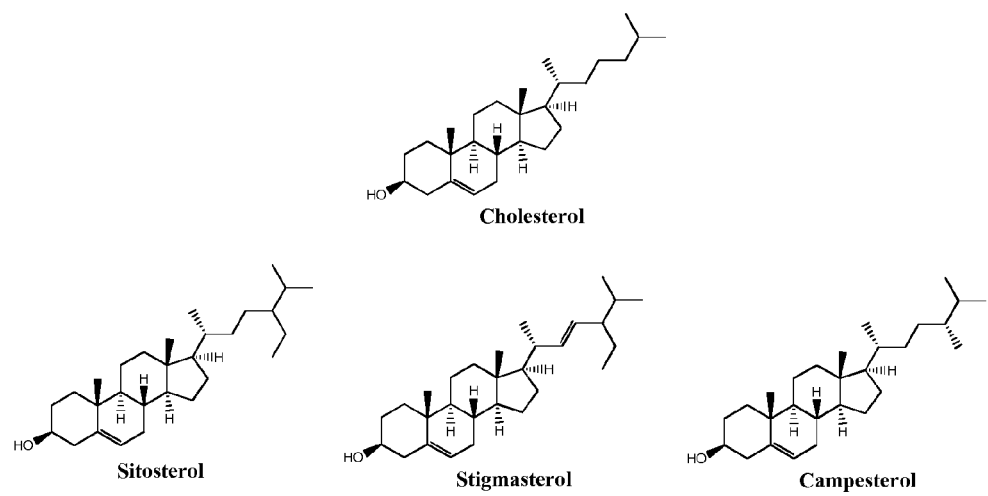
FIG. 1 shows chemical structures of cholesterol, and sitosterol, campesterol or stigmasterol among phytosterols, as examples of compounds to be analyzed from a blood spot in the present disclosure.

The advantages, features and aspects of the present disclosure will become apparent from the following description of the embodiments with reference to the accompanying drawings, which is set forth hereinafter.

In one aspect of this disclosure, there is provided a method for discriminating sitosterolemia by simultaneously measuring concentrations of phytosterols including sitosterol and cholesterol metabolism-related compounds, which includes the following steps:

(a) preparing a paper stained with one drop of blood spot;

(b) extracting sitosterol, campesterol and stigmasterol as phytosterols, and cholesterol metabolism-related compounds from the paper;

(c) evaluating relative metabolic ratios between the above compounds by using gas chromatography-mass spectrometry; and (d) discriminating the case that relative metabolic ratio of sitosterol/cholesterol is about 0.01 or more, that of campesterol/cholesterol is about 0.02 or more, that of stigmasterol/cholesterol is about 0.001 or more, that of campesterol/sitosterol is about 1.0 or less and that of sitosterol/desmosterol is about 100 or more in mass ratio, as sitosterolemia.

The present inventors have conducted intensive researches to develop a method for simply discriminating sitosterolemia. As a result, the present inventors confirmed a method, which may quickly discriminate sitosterolemia with high accuracy by only a single test measuring metabolic ratios between phytosterols and cholesterol metabolism-related compounds with only one drop of blood spot on a paper, as a simple method like blood groups test.

In this description, the term "cholesterol metabolism-related compound" refers to a meaning that includes cholesterol, its metabolites or precursors, and specifically, it may refer to cholesterol, desmosterol, lanosterol, lathosterol, hydroxycholesterol, cholesteryl laurate, cholesteryl myristate or cholesteryl arachidonate.

In this description, the term "phytosterol" refers to all alcohols, which are contained in higher plant life and have steroid backbones, and specifically, it may be sitosterol, campesterol or stigmasterol.

The method of the present disclosure may discriminate sitosterolemia with very high accuracy by measuring relative metabolic ratios between phytosterols (sitosterol, campesterol and stigmasterol), and cholesterol and its metabolites in one drop of blood spot, and specifically, the case when the relative metabolic ratio of sitosterol/cholesterol is about 0.01 or more, that of campesterol/cholesterol is about 0.02 or more, that of stigmasterol/cholesterol is about 0.001 or more, that of campesterol/sitosterol is about 1.0 or less and that of sitosterol/desmosterol is about 100 or more in mass ratio may be discriminated as sitosterolemia.

The method may sufficiently discriminate with only the ratio of the upper limit or the lower limit, and it does not require the separate lower limit or the upper limit clinically. The reason is that when the ratio of sitosterol/cholesterol is less than about 0.01, that of campesterol/cholesterol is less than about 0.02, that of stigmasterol/cholesterol is less than about 0.001, that of campesterol/sitosterol is more than about 1.0 and that of sitosterol/desmosterol is less than about 100, it may be discriminated as normal.

If the ratio specified by the upper limit or the lower limit is specified from the lower limit to the upper limit, for example, sitosterol/cholesterol, campesterol/cholesterol, stigmasterol/cholesterol, campesterol/sitosterol and sitosterol/desmosterol may be specified from about 0.01 to about 0.5, from about 0.02 to about 0.2, from about 0.001 to about 0.02, from about 0.1 to about 1.0 and from about 100 to about 2000, respectively, but not limited thereto, and all ranges out of the normal ratio may be interpreted as the range of sitosterolemia.

This discrimination method measuring the above 5 relative metabolic ratios at the same time may have very high accuracy, compared with the case of discriminating by measuring only the concentration of phytosterol in plasma/serum isolated from a large amount of blood.

Hereinafter, the present disclosure will be described step by step.

Step (a): Preparation of a Paper Stained with One Drop of Blood

The first step is for preparing a paper with one drop of blood spot. The blood spot may be in a state of dried or not dried, and specifically, it may be dried blood spot. In general, when measuring concentration of phytosterol in blood, there is inconvenience that a large amount of blood is collected and the blood is separated into serum or plasma by, for example, centrifugation. However, in the case of the present disclosure, only a trace amount of blood spot is required. Accordingly, the dried blood spot of the present disclosure has advantages of simpler sample collection and easier storage or transfer.

In this description, the term "a trace amount" refers to a unit of below ml, and specifically refers to an amount of below about 100 μl, and more specifically, an amount of about 0.1 to about 50 μl.

Step (b): Extraction of Phytosterol and Cholesterol from the Paper

The second step is for extracting phytosterols including sitosterol, campesterol and stigmasterol, and cholesterol metabolism-related compounds from the blood spotted paper. This extraction may be conducted by using various organic solvents, but it is important to extract without changing the quantitative content ratio of the compounds in the blood spot because the blood spot is in a trace amount. Accordingly, organic solvents, which may extract only a certain sterol or may change the content ratio between sterols by the extraction, may not be used. Specifically, the extraction solvent may be a low grade alcohol having 1 to 4 carbon atoms or a combination thereof, and more specifically, it may be methanol.

When a low grade alcohol having 1 to 4 carbon atoms or a combination thereof is used as an extraction solvent, the extraction may be conducted by using a tissue homogenizer with vibration for about 3 to 7 min at a frequency of about 20 to about 30 times/sec. Here, TissueLyser may be used as the tissue homogenizer.

This step may further include a step of purifying and concentrating the extract by solid phase extraction.

When using the solid phase extraction, the cholesterol and phytosterols may be eluted with a solvent, the solvent may be evaporated by using a nitrogen evaporator, and then dried in a vacuum dryer by using $P_2O_5$/KOH. Specifically, the solvent may be a low grade alcohol having 1 to 4 carbon atoms or a combination thereof.

Step (c): Measurement of Relative Metabolic Ratios Between Cholesterol and Phytosterols Using Gas Chromatography-Mass Spectrometry The third step is for measuring relative metabolic ratios between cholesterol and phytosterols contained in the above extract. For quick and accurate measurement, gas chromatography-mass spectrometry may be used, and may preferably be conducted by reacting the residue dried in the above step with a mixed solution (500:4:5, v/w/w) of MSTFA (N-methyl-N-trifluorotrimethylsilyl acetamide)/$NH_4I$ (ammonium iodide)/dithioerythritol (DTE) for trimethylsilyl derivatization.

Step (d): Discrimination of Sitosterolemia by Using Measured Relative Metabolic Ratios The last step is for discriminating sitosterolemia by analyzing the relative metabolic ratios between phytosterols and cholesterol, which were measured by using gas chromatography-mass spectrometry.

In order to discriminate sitosterolemia by measuring the metabolic ratios between phytosterols such as sitosterol, campesterol and stigmasterol, and cholesterol, the ratio of an accurate range between metabolites is required. Namely, when it is measured as only the absolute amounts of cholesterol or phytosterols, or when it is measured with overlooking structural similarities between cholesterol and phytosterols, there may be a risk of misdiagnosis into hypercholesterolemia or atherosclerosis. And, the accurate and quick discrimination may be possible only when measuring the ratio of phytosterol:cholesterol, and the definite relative ratios between sitosterol, campesterol and stigmasterol, among phytosterols, and cholesterol metabolism-related compounds are accompanied.

For accurate discrimination, the case when the relative metabolic ratios between phytosterols and cholesterol metabolism-related compounds, i.e., the ratio of sitosterol/cholesterol is about 0.01 or more, that of campesterol/cholesterol is about 0.02 or more, that of stigmasterol/cholesterol is about 0.001 or more, that of campesterol/sitosterol is about 1.0 or less and that of sitosterol/desmosterol in mass ratio is about 100 more may be discriminated as a metabolic disorder.

EXAMPLES

Hereinafter, the present disclosure will now be described in further detail by examples. It would be obvious to those skilled in the art that these examples are intended to be more concretely illustrative and the scope of the present disclosure as set forth in the appended claims is not limited to or by the examples.

Example 1

1) Extraction

A blood spot collected on a piece of paper was cut into a circular shape, placed into a test tube with methanol 0.5 mL and an internal standard material 20 µL, and then the compounds in the blood spot, desired to be analyzed, were extracted with TissueLyser (Qiagen, USA) by shaking for about 5 min at a frequency of 25 times/sec.

2) Solid Phase Extraction

Hybrid SPE-Phospholipid cartridge [30 mg/1 mL, Supelco, USA] was used for solid phase extraction. The extract from the above 1) was flowed into the cartridge so as to remove analysis interfering substances such as lipids, and methanol 0.5 mL was flowed thereinto a total of 3 times to elute phytosterols and cholesterol metabolism-related compounds as analytes followed by collecting thereof into a clear test tube. Then, the solvent contained in the eluted solution was evaporated at 40° C. by using a nitrogen evaporator, and then fully dried using $P_2O_5$/KOH in a vacuum dryer for at least 30 min.

3) Gas Chromatography-Mass Spectrometry

For effective gas chromatography-mass spectrometry, a mixed solution (500:4:5, v/w/w) of MSTFA (N-methyl-N-trifluorotrimethylsilyl acetamide)/$NH_4I$ (ammonium iodide)/dithioerythritol (DTE) 40 µL was added to the residue dried according to the description of the above 2), and then reacted at 60° C. for 20 min for trimethylsilyl derivatization.

The gas chromatography-mass spectrometer used for the analysis was 6890 series Gas Chromatograph connected with 5975C Mass Selective Detector of Agilent Technologies, and selected-ion monitoring mode (SIM) for selectively detecting only specific ions was used. Further, the column used for the analysis was MXT-5 of Restek Corporation made of a stainless material coated with stationary phase, wherein 95% polydimetylsiloxane was cross-linked with 5% polydiphenylsiloxane, a column with a length of 15 m, an internal diameter of 0.25 mm and 0.25 µm of film thickness. The temperature at an inlet was 300° C., and 2 µL of a sample was injected via split injection of 10:1 and then analyzed. The temperature condition of an oven was maintained at 265° C. for 5 min, heated to 280° C. at a rate of 2° C./min, and then heated to 380° C. at a rate of 10° C./min and maintained at the temperature for 3 min. As a method of ionizing the analytes, electron impact ionization (EI) of 70 eV was used. An ion source for ionization was kept at 230° C., and a detector was maintained at 250° C. The analytes were confirmed by comparing the ratio of peak heights of two specific ions and retention time in a column with reference to each standard material.

4) Evaluation of Concentration of Analytes

In order to evaluate concentrations of cholesterol and phytosterols in the sample collected from the dried blood spot, test samples were prepared by taking standard solutions of each compound by concentration, based on 20 µL of a blood sample. Then, the test samples were identically treated with real clinical samples according to the description mentioned in 1), 2) and 3) followed by plotting a calibration curve through the ratio of peak height of each compound and peak height of the internal standard material. The concentration of each compound was measured by substituting the ratio of the compound detected from the test sample to the internal standard material, to an equation, $y=ax+b$, obtained from the plotted calibration curve.

However, because it is difficult to determine the exact amount of the collected sample used in the test, relative metabolic ratios between metabolites were evaluated by using the measured concentration of each compound.

Test Example 1

Relative concentrations of phytosterols and cholesterol metabolism-related compounds were measured by using blood spots collected from 3 sitosterolemia patients and 4 normal individuals through the analyzing method of Example 1, and the results are shown in Table 1.

It was confirmed that the concentrations of cholesterol and desmosterol were similar in both of the patient group and the normal group, but the concentrations of phytosterols, i.e., sitosterol, campesterol and stigmasterol, were much higher in the patient group than the normal group.

TABLE 1

Relative concentrations of phytosterols and cholesterol metabolism-related compounds in the patient group and the normal group

| Compound | Concentration (μg in collected blood spot) | | | | | | |
| --- | --- | --- | --- | --- | --- | --- | --- |
| | Patient 1 | Patient 2 | Patient 3 | Normal 1 | Normal 2 | Normal 3 | Normal 4 |
| Cholesterol | 1003.4 | 1102.5 | 982.0 | 1206.0 | 1189.7 | 1318.7 | 1134.0 |
| Sitosterol | 192.8 | 253.1 | 173.1 | 3.9 | 2.8 | 6.4 | 6.2 |
| Campesterol | 91.6 | 121.9 | 105.9 | 5.9 | 5.2 | 11.3 | 11.4 |
| Stigmasterol | 8.3 | 15.2 | 9.5 | 0.6 | 0.6 | 0.6 | 0.7 |
| Desmosterol | 0.2 | 0.5 | 0.3 | 0.2 | 0.4 | 0.3 | 0.5 |
| 7-Dehydro cholesterol | 0.1 | 0.2 | 0.2 | 0.3 | 0.3 | 0.3 | 0.4 |
| Lathosterol | 0.7 | 1.3 | 2.7 | 1.8 | 1.3 | 2.1 | 4.1 |
| Lanosterol | 0.1 | 0.1 | 0.2 | 0.1 | 0.1 | 0.1 | 0.3 |
| 7α-Hydroxy cholesterol | 1.0 | 1.0 | 1.6 | 1.2 | 1.8 | 1.8 | 4.0 |
| 7β-Hydroxy cholesterol | 2.3 | 2.6 | 2.9 | 2.7 | 3.2 | 3.7 | 7.7 |
| 4β-Hydroxy cholesterol | 0.2 | 0.1 | 0.1 | 0.2 | 0.2 | 0.2 | 0.3 |
| 27-Hydroxy cholesterol | 0.1 | Not Detected | 0.1 | 0.1 | 0.1 | 0.1 | 0.1 |
| 24-Hydroxy cholesterol | 0.1 | 0.2 | 0.1 | 0.1 | 0.1 | 0.1 | 0.1 |
| 25-Hydroxy cholesterol | 0.1 | 0.1 | 0.1 | 0.1 | 0.1 | 0.1 | 0.1 |
| Cholesteryl laurate | 0.6 | 0.8 | 1.6 | 1.0 | 0.6 | 2.0 | 1.1 |
| Cholesteryl myristate | 43.5 | 54.8 | 52.5 | 25.4 | 14.0 | 96.5 | 22.0 |
| Cholesteryl arachidonate | 112.7 | 91.3 | 93.5 | 105.4 | 73.2 | 185.4 | 89.4 |

Test Example 2

Figure 2A:
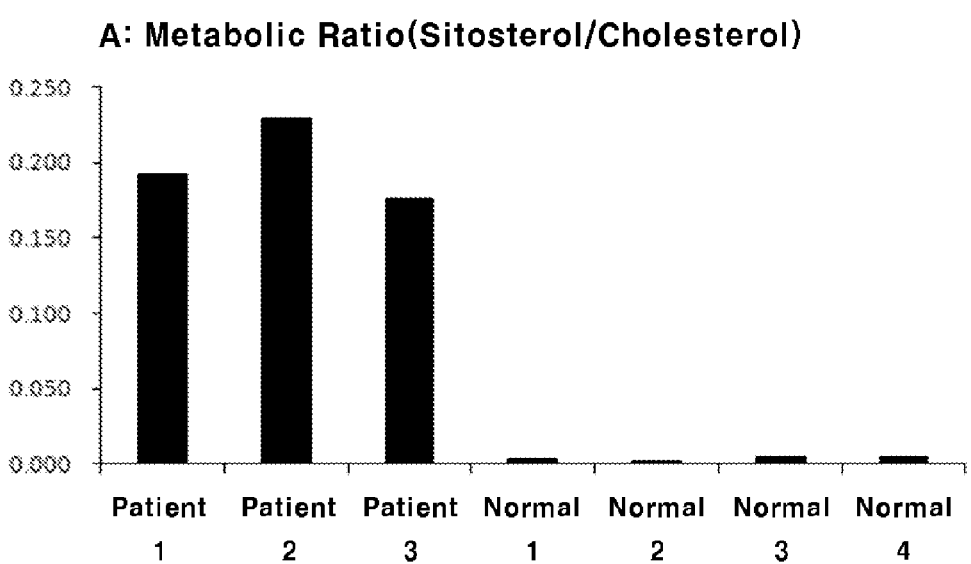
FIG. 2 shows results of evaluating metabolic correlations of compounds measured from the blood spot through the present disclosure, and includes graphs illustrating a ratio of sitosterol to cholesterol (FIG. 2*a*); a rate of campesterol to cholesterol (FIG. 2*b*); ratio of stigmasterol to cholesterol (FIG. 2*c*); a ratio between phytosterols, i.e., sitosterol and campesterol (FIG. 2*d*); and a metabolic ratio between desmosterol, a metabolic precursor of cholesterol, and sitosterol (FIG. 2*e*) in a normal group and a patent group.
Figure 2B:
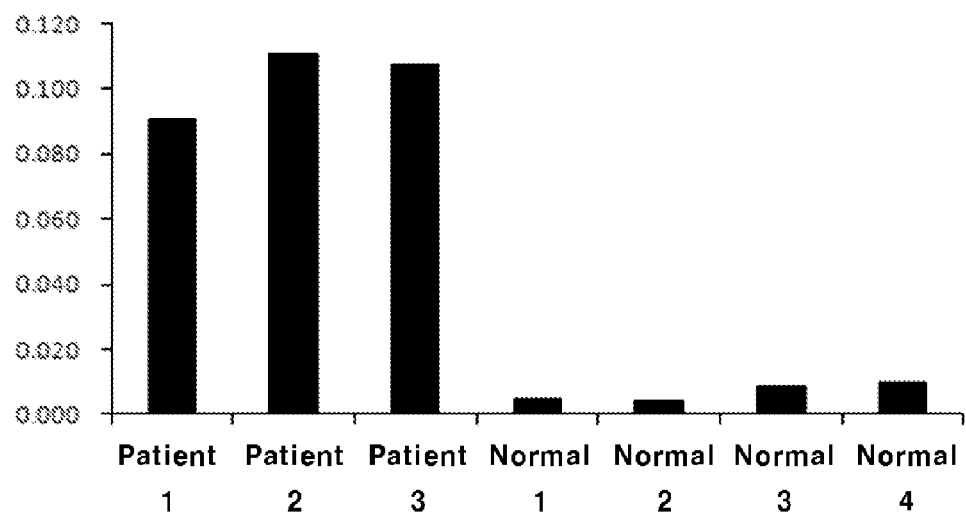
Figure 2C:
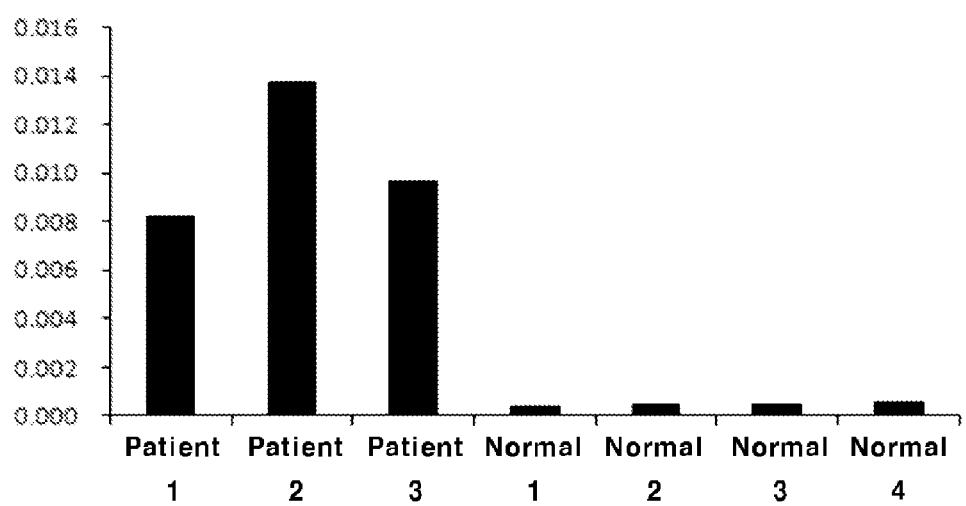
Figure 2D:
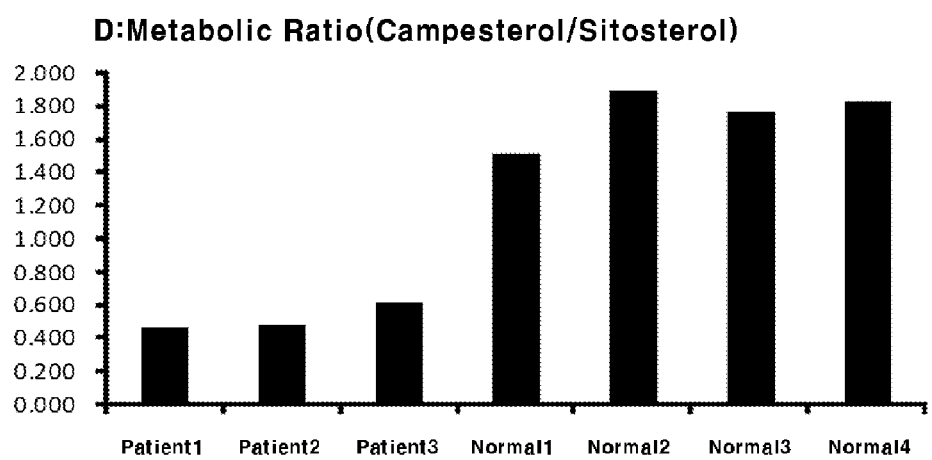
Figure 2E:
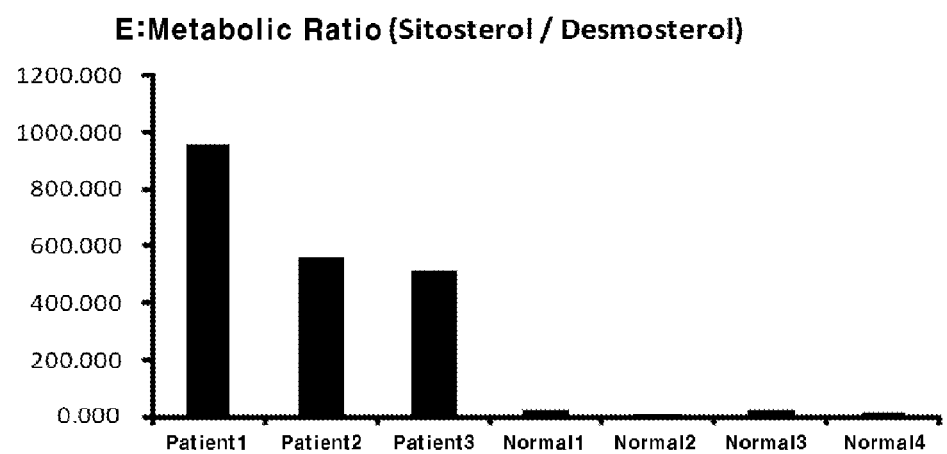

Metabolic ratios between the compounds were evaluated by the measured concentrations of phytosterols, i.e., sitosterol, stigmasterol and campesterol, and cholesterol metabolism-related compounds in the blood spot, and the results are shown in FIGS. 2a to 2e. It was confirmed that there is a big difference between the metabolic ratios between phytosterols to cholesterol, and between phytosterols in the patient group and the normal group.

The features and advantages of the present disclosure will be summarized as follows:

(i) The present disclosure provides a method for discriminating sitosterolemia by simultaneously measuring relative concentrations of phytosterols and cholesterol in a blood spot.

(ii) According to the present disclosure, sitosterolemia may be quickly discriminated with high accuracy by simple sample collecting using a trace amount of blood spot stained on a paper, and it may be used for newborn screening and preschool children, particularly patients with xanthoma, accompanied by blood groups test.

While the present disclosure has been described with respect to the specific embodiments, it will be apparent to those skilled in the art that various changes and modifications may be made without departing from the spirit and scope of the disclosure as defined in the following claims.

What is claimed is:

1. A method for discriminating sitosterolemia comprising the following steps:
preparing a piece of paper stained with one drop of blood spot;
extracting sitosterol, campesterol and stigmasterol as phytosterols, and cholesterol metabolism-related compounds from the paper;
evaluating relative metabolic ratios between the above compounds by using gas chromatography-mass spectrometry; and
discriminating the case that relative metabolic ratio of sitosterol/cholesterol is about 0.01 or more, that of campesterol/cholesterol is about 0.02 or more, that of stigmasterol/cholesterol is about 0.001 or more, that of campesterol/sitosterol is about 1.0 or less and that of sitosterol/desmosterol is 100 or more in mass ratio, as sitosterolemia.

2. The method according to claim 1, wherein the relative metabolic ratio of sitosterol/cholesterol is about 0.01 to about 0.5, that of campesterol/cholesterol is about 0.02 to about 0.2, that of stigmasterol/cholesterol is about 0.001 to about 0.02, that of campesterol/sitosterol is about 0.1 to about 1.0 and that of sitosterol/desmosterol is about 100 to about 2000 in mass ratio.

3. The method according to claim 1, wherein the extracting is conducted with a low grade alcohol having 1 to 4 carbon atoms by using a tissue homogenizer with vibration for about 3 to about 7 min at a frequency of about 20 to about 30 times/sec.

4. The method according to claim 1, wherein the extracting step may further comprise a step of purifying and concentrating the extract by solid phase extraction.

5. The method according to claim 4, wherein the solid phase extraction is conducted by eluting sitosterol, campesterol and stigmasterol as phytosterols, and cholesterol metabolism-related compound with a solvent; evaporating the solvent by using a nitrogen evaporator; and then drying thereof in a vacuum dryer by using $P_2O_5$/KOH.

6. The method according to claim 1, wherein the gas chromatography-mass spectrometry is conducted by reacting the dried residue of claim 5 with a mixed solution (500:4:5, v/w/w) of MSTFA (N-methyl-N-trifluorotrimethylsilyl acetamide)/$NH_4I$ (ammonium iodide)/dithioerythritol (DTE) for trimethylsilyl derivatization.

* * * * *